US008348848B1

(12) United States Patent
Tamura

(10) Patent No.: US 8,348,848 B1
(45) Date of Patent: Jan. 8, 2013

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 73 days.

(21) Appl. No.: 13/079,499

(22) Filed: Apr. 4, 2011

Related U.S. Application Data

(60) Provisional application No. 61/410,090, filed on Nov. 4, 2010.

(51) Int. Cl.
*A61B 8/00* (2006.01)

(52) U.S. Cl. .......................... 600/444; 600/441; 600/443

(58) Field of Classification Search ........... 600/437–469
See application file for complete search history.

(56) References Cited

U.S. PATENT DOCUMENTS

| 6,423,004 | B1 | 7/2002 | Dong et al. | |
|---|---|---|---|---|
| 6,547,732 | B2 * | 4/2003 | Jago | 600/437 |
| 6,719,693 | B2 * | 4/2004 | Richard | 600/437 |
| 6,843,770 | B2 | 1/2005 | Sumanaweera | |
| 7,600,689 | B2 * | 10/2009 | Tsikos et al. | 235/462.43 |
| 7,819,805 | B2 * | 10/2010 | Davies et al. | 600/437 |
| 7,850,611 | B2 * | 12/2010 | Davies et al. | 600/447 |
| 2001/0014773 | A1 * | 8/2001 | Jago | 600/437 |
| 2003/0187357 | A1 * | 10/2003 | Richard | 600/437 |
| 2004/0077946 | A1 * | 4/2004 | Ohmiya | 600/437 |
| 2006/0058670 | A1 * | 3/2006 | Lin et al. | 600/447 |
| 2007/0167823 | A1 * | 7/2007 | Lee et al. | 600/463 |
| 2008/0287799 | A1 * | 11/2008 | Hall et al. | 600/454 |
| 2011/0066032 | A1 * | 3/2011 | Vitek et al. | 600/459 |

OTHER PUBLICATIONS

M. Berson et al., "Compound Scanning With an Electrically Steered Beam", Ultrasonic Imaging, vol. 3, Issue 3, Jul. 1981, (pp. 303-308, total 6 pages).

* cited by examiner

*Primary Examiner* — Sanjay Cattungal
(74) *Attorney, Agent, or Firm* — Buckley, Maschoff & Talwalkar LLC

(57) ABSTRACT

Systems and methods are described to determine a region of interest, determine a first beam steering angle of a first ultrasound beam transmitted from an ultrasound transducer array that results in a maximum representative signal value received from the region of interest, determine a second beam steering angle based on the first beam steering angle, the second beam steering angle being closer to perpendicular with the ultrasound transducer array than the first beam steering angle, and acquire an ultrasound image using a beam transmitted from the ultrasound transducer array at the second beam steering angle.

24 Claims, 4 Drawing Sheets

METHODS AND APPARATUS FOR ULTRASOUND IMAGING

CROSS-REFERENCE TO RELATED APPLICATION

The present application claims priority to U.S. Provisional Patent Application Ser. No. 61/410,090, filed on Nov. 4, 2010 and entitled "Method and Apparatus for Ultrasound Imaging", the contents of which are incorporated herein by reference for all purposes.

BACKGROUND

Systems and methods described herein generally relate to the field of medical ultrasound imaging. More specifically, embodiments described below relate to methods and systems which may be employed to generate images of interventional devices such as biopsy needles.

Conventional ultrasound imaging may be used to produce images of internal biological tissue structures. These images may be used to detect and diagnose internal abnormalities, to assist in medical interventions (e.g., real-time viewing of a needle during a biopsy procedure), or for any other purpose. Under many conditions, conventional ultrasound imaging produces images which are suitable for their intended purpose. However, under certain conditions and/or for certain purposes, images produced by conventional ultrasound imaging are not satisfactory.

FIG. 1 illustrates ultrasound imaging of a medical intervention. The area 150 includes internal tissue and a target lesion 140. During a biopsy, the biopsy needle 120 is inserted into the tissue from the skin surface to the target lesion 140 and under the ultrasound transducer 110. The needle 120 is therefore tilted with respect to the skin surface and the transducer 110.

To acquire a B-mode image, ultrasound beams are transmitted directly downward from the transducer 110 with no beam steering (0 degrees) and resulting ultrasound beams are then received by the transducer 110. Although only one ultrasound beam 170 is shown in FIG. 1, multiple ultrasound beams (e.g., a few hundred) may be transmitted. A B-mode image of the area 150 may then be created based on the received beams using known techniques.

The reflectivity of the needle at the illustrated entry angle is lower than the reflectivity of the needle if entering parallel to the transducer 110. Therefore, as shown in FIG. 1, an ultrasound image of the needle 130 will appear faint in the resulting B-mode image 150. As a result, it is difficult to guide the biopsy based on the B-mode image 150.

DETAILED DESCRIPTION

Embodiments will be described with reference to the accompanying drawing figures wherein like numbers represent like elements throughout. Before embodiments are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

Some embodiments relate to the acquisition of an ultrasound image using one or more ultrasound beams. As is known, an ultrasound image of an area may be obtained by transmitting an ultrasound beam from an ultrasound transducer array into the area at a beam steering angle and by receiving ultrasound beams scattered by tissue within the area.

A method to improve ultrasound imaging according to some embodiments will now be described. Initially, the beam steering angle is varied until a maximum signal is obtained from a region of interest (e.g., a region in which a biopsy needle resides). The steering angle at which such a maximum representative signal is obtained may position the ultrasound beam axis at about 90 degrees to the axis of the biopsy needle.

Figure 2A:
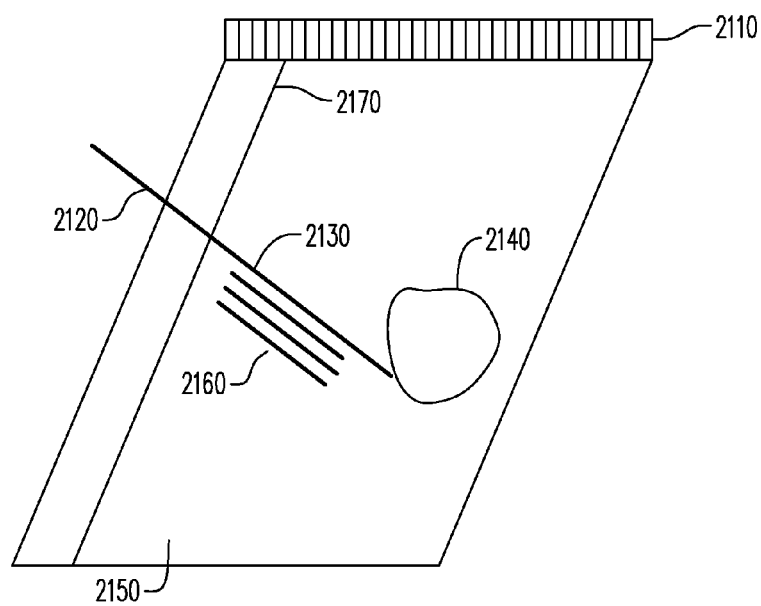
FIG. 2A. An ultrasound image using a beam steering angle (e.g. 20 degrees).
Figure 2B:
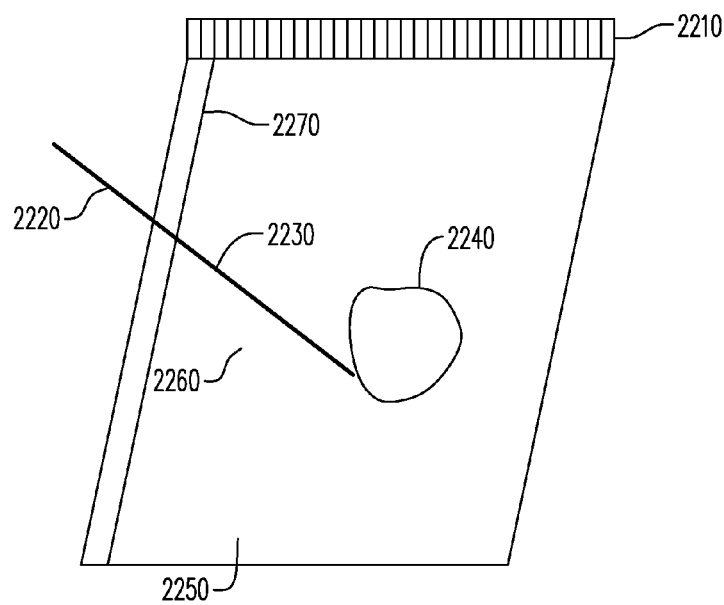
FIG. 2B. An ultrasound image using a beam steering angle which is slightly smaller than the angle in FIG. 2A.

According to the convention used herein, and with respect to the ultrasound images illustrated in FIGS. 2A and 2B, a beam steering angle of 0 degrees refers to a beam which proceeds perpendicularly from the transducer array (e.g., with reference to FIG. 2B, vertically from the transducer to the bottom of the image). A beam steering angle of 20 degrees refers to a beam steered 20 degrees to the left of a 0 degree beam, while a beam steering angle of −20 degrees refers to a beam steered 20 degrees to the right of a 0 degree beam.

Figure 1:
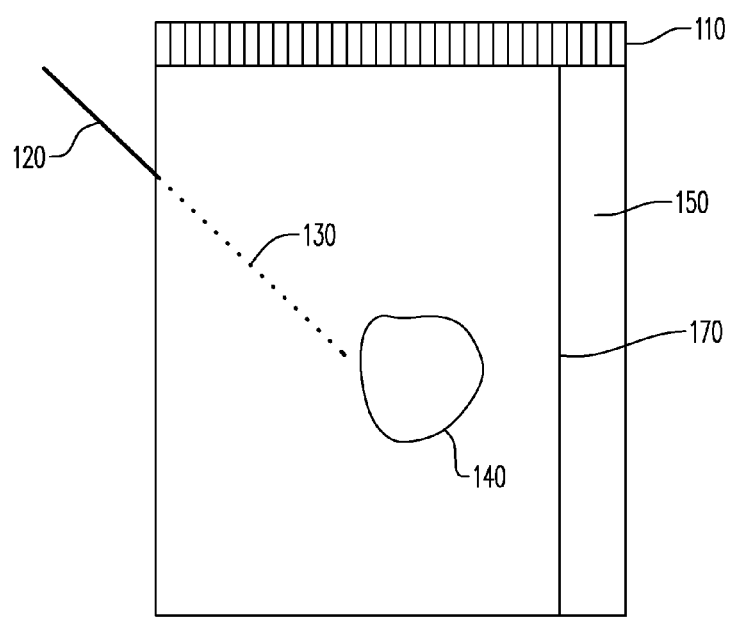
FIG. 1. A conventional ultrasound image of a biopsy needle.

FIG. 2A shows an internal tissue area 2150 including a biopsy needle 2120 and a target lesion 2140. An ultrasound image of area 2150 is acquired using an ultrasound transducer 2110 comprising an array of elements and an ultrasound beam transmitted from the transducer array at a beam steering angle of, e.g., 20 degrees to the left. One ultrasound beam 2170 is shown as an example although multiple ultrasound beams (e.g. a few hundred) may be used to acquire the image. Since the ultrasound beams are steered to the left and the angle between the ultrasound beams and the needle axis is close to 90 degrees, the needle 2130 reflects the ultrasound beam fairly well. Accordingly, the needle 2130 may be more visible in the resulting image 2150 of FIG. 2A than in the image 150 of FIG. 1. However, the ultrasound image 2150 shows strong reverberation noise 2160 in the lower side of the needle image 2130.

Therefore, in some embodiments, an ultrasound image is obtained using a beam steering angle which is offset by some small angle from the angle at which the maximum representative signal is obtained. Generally, the new beam steering angle has a smaller absolute value than the angle at which the maximum signal is obtained. FIG. 2B shows such a beam angle condition within an ultrasound image 2250. Using the new beam steering angle, the needle 2220 images well, and reverberation noise 2260 is reduced or eliminated as shown in FIG. 2B.

Prior to the foregoing steps, the region of interest may be pre-set or may be defined by the user. The whole ultrasound image area may be selected as the region of interest, or a part of the whole image area may be selected as the region of interest. The region of interest may be pre-set in a region where a biopsy needle may be most-likely located in the medical procedure (e.g., a central region under the ultrasound probe, as the medical provider likes to position the biopsy needle in the center of an ultrasound image). The region of interest may be automatically set in a region where the ultrasound signal is large since the large ultrasound signal may indicate a presence of a biopsy needle.

In order to determine the beam steering angle which results in the maximum representative signal from the region of interest, one or more ultrasound beams are transmitted at a first beam steering angle and a corresponding signal value from the region of interest is determined for the first beam steering angle. The beam steering angle is varied and the process is repeated for as many beam steering angles as desired. The beam steering angle which resulted in the maximum representative signal value is then identified.

During the determination of the beam steering angle which results in the maximum signal from the region of interest, the beam steering angle may be varied at a fixed angular increment, for example, 5 degrees. The beam steering angle may be varied from the left-most angle (e.g., 30 degrees) to the right-most angle (e.g., −30 degrees), or vice versa. Or the beam steering angle may be varied from 0 degrees to the left-most angle and/or the beam steering angle may be varied from 0 degrees to the right-most angle. Alternately, the beam steering angle may be varied at random. The beam steering angle may be varied at other fixed or variable angular increments (e.g., 5 degrees, 10 degrees or other values). The beam steering angle may be varied to acquire an ultrasound image for each of a set of beam steering angles stored in memory.

The representative signal value from the region of interest corresponding to a given beam steering angle may be determined as the mean of ultrasound image signals in the region of interest. Other statistical values such as mode, median, maximum, a percentile value (e.g., 80% percentile) may be used to determine a representative signal value corresponding to a beam steering angle in a region of interest.

In some embodiments of the foregoing determination, the ultrasound signal from the region of interest is monitored while the beam steering angle is varied, and the ultrasound signal's angle derivative is determined. If the angle derivative exhibits positive values prior to reaching 0, it is determined that the ultrasound signal is the maximum at the point where the signal's angle derivative is 0. The beam steering angle at this point is therefore selected as the beam steering angle that results in the maximum representative signal value.

Next, as described with respect to FIG. 2B, an ultrasound image is obtained using a second beam steering angle which is closer to perpendicular with the transducer array than the beam steering angle at which the maximum representative signal is obtained.

Using the above-described convention, this second beam steering angle is smaller (in absolute value) than the beam steering angle at which the maximum representative signal is obtained. For example, if the beam steering angle at which the maximum signal is obtained is 20 degrees, the ultrasound image may be obtained using a 15 degree beam steering angle. If the beam steering angle at which the maximum representative signal is obtained is −20 degrees, the ultrasound image may be obtained using a −15 degree beam steering angle. In another example, the beam steering angle at which the maximum signal is obtained is −5 degrees, and the ultrasound image is obtained using a 0 degree beam steering angle.

In some embodiments, a first ultrasound image $I_{1,x,y}$ acquired at the second beam steering angle which is smaller (in absolute value) than the beam steering angle at which the maximum representative signal is obtained may be combined with an ultrasound image $I_{2,x,y}$ acquired at a smaller in absolute value, including 0 degree beam steering angle to create a second output image $I_{x,y}$ where x, y are a coordinate of an image pixel position. Such embodiments may be advantageous because the ultrasound image at such a smaller beam steering angle may provide better image quality in areas other than the biopsy needle, and provides a wide image field. The first ultrasound image $I_{1,x,y}$ and the image generated using the absolute smaller or no steering angle $I_{2,x,y}$ may be summed using weights as follows:

$$I_{x,y} = w_{1,x,y} \cdot I_{1,x,y} + w_{2,x,y} \cdot I_{2,x,y},$$

where $w_{1,x,y}$ and $w_{2,x,y}$ are fixed values and may be identical to or different from one another. Furthermore the weights may depend on image values at each image pixel location as follows, $$w_{1,x,y} = f(I_{1,x,y}, I_{2,x,y}),$$

$$w_{2,x,y} = g(I_{1,x,y}, I_{2,x,y}),$$

where $w_{1,x,y}$ is a weight of the first image at (x, y), while $w_{2,x,y}$ is a weight of the ultrasound image generated using the absolute smaller beam steering angle or no beam steering at (x, y). $f(I_{1,x,y}, I_{2,x,y})$ and $g(I_{1,x,y}, I_{2,x,y})$ are functions of $I_{1,x,y}$ and $I_{2,x,y}$ (i.e., image values at (x, y) of the first output image and the second image acquired at a beam steering angle substantially perpendicular to the ultrasound transducer array).

The ultrasound signal may be an RF-signal, an IF signal, a demodulated baseband signal, line (i.e., beam) data, or a scan-converted B-mode image signal.

Figure 3:
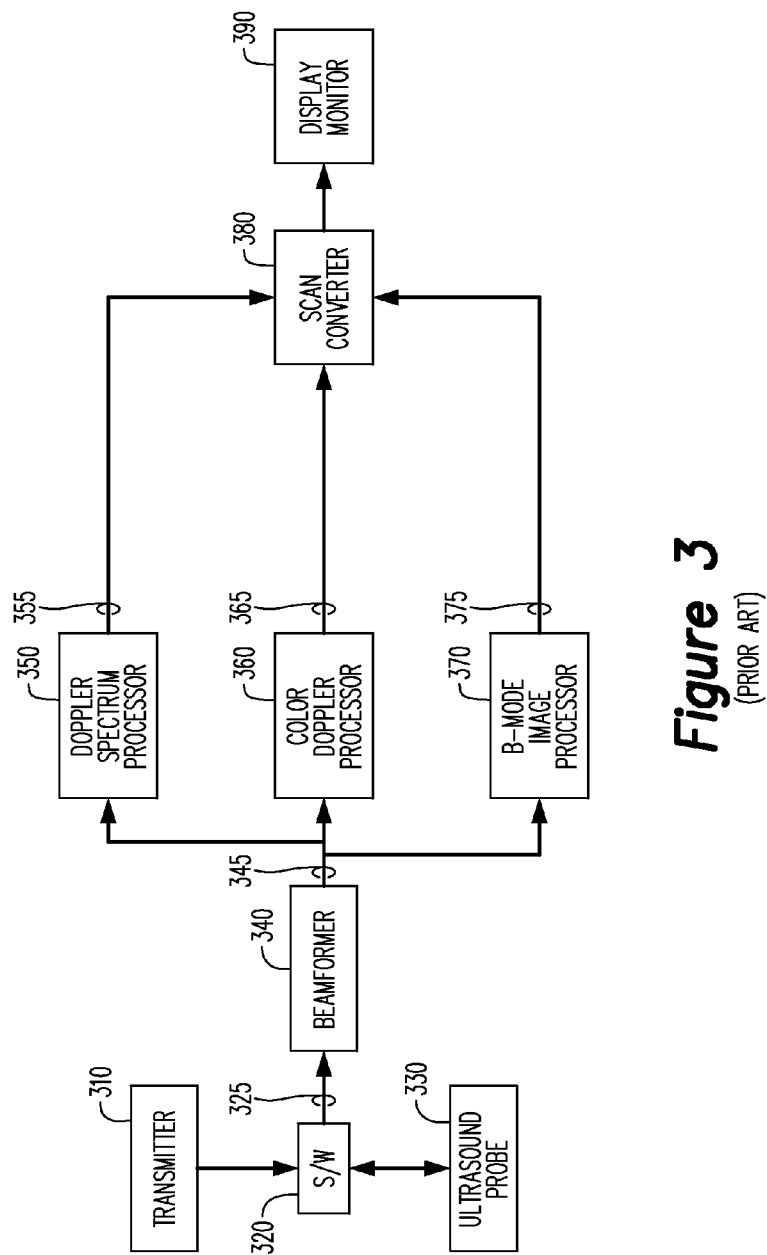
FIG. 3. A diagram of a conventional ultrasound imaging system.

FIG. 3 shows a diagram of a conventional ultrasound diagnostic imaging system with B-mode imaging, Doppler spectrum and color Doppler imaging. The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter/transmit beamformer 310 through a transmit/receive switch 320. The probe 320 may consist of an array of transducer elements which are separately driven by the transmitter/transmit beamformer 310 with different time-delays so that a transmit ultrasound beam is focused and steered in tissue. The transmitted ultrasound beam (or signal) is scattered by the tissue and scattered ultrasound signals are returned to the probe 330. The probe then receives the ultrasound signals from the tissue and a receive beamformer 340 receives the received ultrasound signals from the probe 330 through the switch 320 and processes the signals 325. The receive beamformer 340 applies delays and/or phases to the signals 325 and the resultant signals are summed for focusing and steering a receive ultrasound beam. The receive beamformer 340 may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal

345 and calculates and outputs a B-mode image 375 or the amplitude of the signal by amplitude detection.

The Doppler spectrum signals 355, color Doppler processor signals (velocity, power, and variance) 365 and B-mode processor signals 375 are coupled to a scan converter 380 that converts the signals to scan-converted signals. For the B-mode signals, the data from the B-mode image processor 375 are line data which consist of processed beam signals for each receive ultrasound beam and may not have signals for all image pixels with the correct vertical-to-horizontal distance relationship for the display. The scan converter 380 interpolates the line data in two dimensions (x, y) and fills in all image pixels with ultrasound image data. The output of the scan converter 380 is coupled to a display monitor 390 for displaying ultrasound images.

Figure 4:
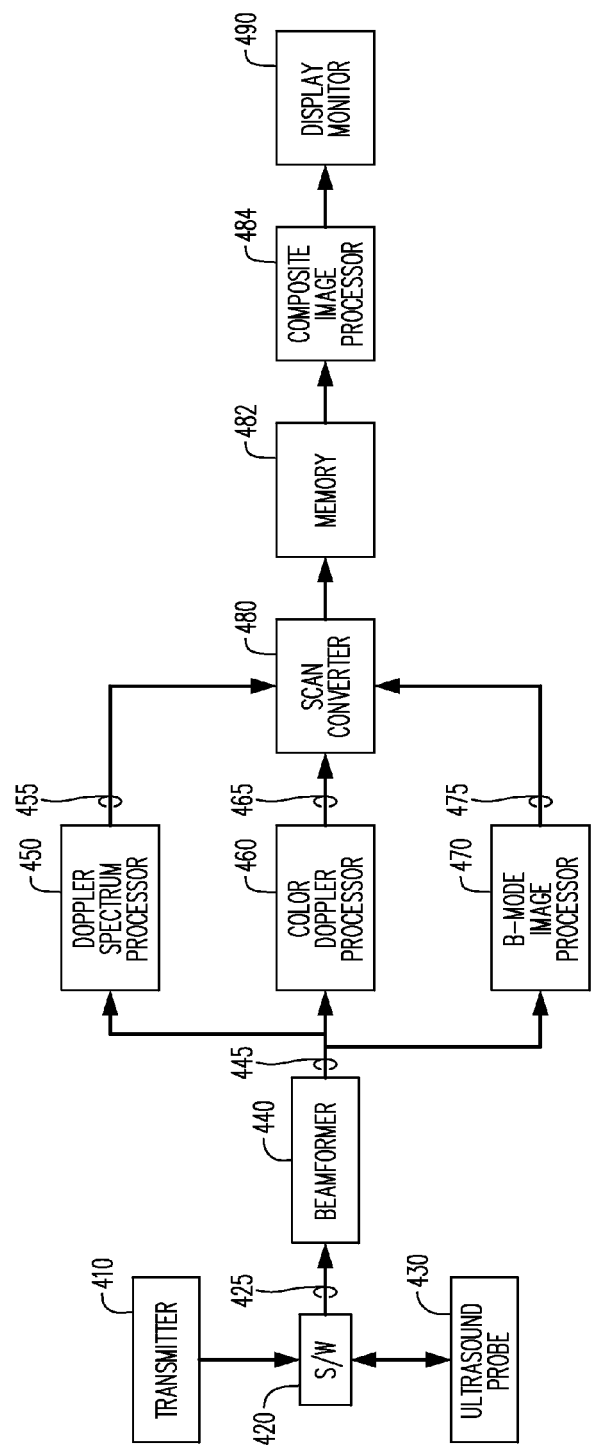
FIG. 4. A diagram of an ultrasound imaging system including a composite image processor according to some embodiments.

FIG. 4 shows a diagram of an ultrasound imaging system of the present invention including a composite image processor 484 for improved imaging, such as, but not limited to, improved visualization of interventional devices such as biopsy needles. The composite image processor 484 may combine a B-mode ultrasound image generated as described above with a B-mode ultrasound image acquired at a smaller (i.e., absolute value) beam steering angle, with or without weights as described above. The resulting image, consisting of a single image pixel value for each of a plurality of image pixel locations, is output to the display monitor 490.

In an alternate embodiment, the composite image processor 484 calculates a new representative ultrasound signal value in the region of interest at a beam steering angle and compares the representative ultrasound signal value with a maximum representative signal value previously obtained at a different beam steering angle and stored in memory. If the new representative ultrasound signal value is greater than the previously-obtained and stored signal value, the stored maximum ultrasound signal value is replaced with the newly-obtained maximum ultrasound signal value, and the newly-obtained maximum ultrasound signal value and its corresponding beam steering angle are also recorded.

Once the maximum representative signal is obtained, the absolute value of the beam steering angle is decreased (i.e., moved closer to vertical) to acquire a first ultrasound image which exhibits better image quality with less reverberations. Next, the beam steering angle is changed to 0 degrees or another angle with a small absolute value to acquire a second ultrasound image at the changed steering angle, which may provide a best quality image in areas other than the needle. The first and second images are then combined, using fixed weighting, or other weightings as described above, to create the output image which is then sent to the display monitor for display.

The transmitter 410 may contain a transmit beamformer which applies time delays to signals for transducer elements for focusing and beam steering. After an ultrasound image is acquired and its representative ultrasound signal in the region of interest is calculated, a set of time delays are either generated or read from memory and loaded to a transmit delay table in order to acquire another ultrasound image using a next transmit beam steering angle. Likewise, the receive beamformer updates the receive time delays in a receive delay table of the receive beamformer 440 in accordance with the next transmit beam steering angle.

The composite image processor 484 may be comprised of general purpose central processing units (CPUs), digital signal processors (DSPs), field programmable Arrays (FPGAs), graphic processing units (GPUs) and/or discreet electronic devices.

FIG. 4 represents a logical architecture according to some embodiments, and actual implementations may include more or different elements arranged in other manners. Other topologies may be used in conjunction with other embodiments. Moreover, each element of the FIG. 4 system may be implemented by any number of computing devices in communication with one another via any number of other public and/or private networks. Two or more of such computing devices may be located remote from one another and may communicate with one another via any known manner of network(s) and/or a dedicated connection. The system may comprise any number of hardware and/or software elements suitable to provide the functions described herein as well as any other functions. For example, any computing device used in an implementation of the FIG. 4 system may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Blu-ray disk, a Flash drive, magnetic tape, and solid state Random Access Memory (RAM) or Read Only Memory (ROM) storage units. Embodiments are therefore not limited to any specific combination of hardware and software.

One or more embodiments have been described. Nevertheless, various modifications will be apparent to those in the art.

The invention claimed is:

1. A method of creating an ultrasound image, comprising:
determining a region of interest;
determining a first beam steering angle of a first ultrasound beam transmitted from an ultrasound transducer array that results in a maximum representative signal value received from the region of interest;
determining a second beam steering angle based on the first beam steering angle, the second beam steering angle being closer to perpendicular with the ultrasound transducer array than the first beam steering angle;
acquiring an ultrasound image using a beam transmitted from the ultrasound transducer array at the second beam steering angle;
acquiring a second ultrasound image using a beam transmitted from the ultrasound transducer array at a third beam steering angle, the third beam steering angle being closer to perpendicular with the ultrasound transducer array than the second beam steering angle; and
combining the ultrasound image and the second ultrasound image to generate a third ultrasound image.

2. A method according to claim 1, wherein the region of interest is pre-set or defined by the user.

3. A method according to claim 1, wherein the representative signal value is one of mean, mode, median, percentile value or other statistical values.

4. A method according to claim 1, wherein determining the first beam steering angle comprises varying a beam steering angle at a fixed angular increment or a variable angular increment.

5. A method according to claim 1, wherein the representative signal value is one of RF-signal, IF signal, demodulated baseband signal, line (i.e., beam) data, or scan-converted B-mode image signal.

6. A method according to claim 1, further comprising combining the ultrasound image and the second ultrasound image with weights.

7. A method according to claim 6, wherein the weights are dependent on the image pixel signals at each image pixel location.

8. A method according to claim 1, wherein determining the first beam steering angle is based on the derivative of the representative signal value.

9. A non-transitory medium storing processor-executable program code, the program code executable by a device to:
   determine a region of interest;
   determine a first beam steering angle of a first ultrasound beam transmitted from an ultrasound transducer array that results in a maximum representative signal value received from the region of interest;
   determine a second beam steering angle based on the first beam steering angle, the second beam steering angle being closer to perpendicular with the ultrasound transducer array than the first beam steering angle;
   acquire an ultrasound image using a beam transmitted from the ultrasound transducer array at the second beam steering angle;
   acquire a second ultrasound image using a beam transmitted from the ultrasound transducer array at a third beam steering angle, the third beam steering angle being closer to perpendicular with the ultrasound transducer array than the second beam steering angle; and
   combine the ultrasound image and the second ultrasound image to generate a third ultrasound image.

10. A medium according to claim 9, wherein the region of interest is pre-set or defined by the user.

11. A medium according to claim 9, wherein the representative signal value is one of mean, mode, median, percentile value or other statistical values.

12. A medium according to claim 9, wherein determination of the first beam steering angle comprises varying a beam steering angle at a fixed angular increment or a variable angular increment.

13. A medium according to claim 9, wherein the representative signal value is one of RF-signal, IF signal, demodulated baseband signal, line (i.e., beam) data, or scan-converted B-mode image signal.

14. A medium according to claim 9, the program code further executable by a device to:
   combine the ultrasound image and the second ultrasound image with weights.

15. A medium according to claim 14, wherein the weights are dependent on the image pixel signals at each image pixel location.

16. A medium according to claim 9, wherein determination of the first beam steering angle is based on the derivative of the representative signal value.

17. A system comprising:
   an ultrasound transducer comprising an array of transducer elements;
   a memory storing processor-executable program code; and
   a processor to execute the processor-executable program code in order to cause the system to:
   determine a region of interest;
   determine a first beam steering angle of a first ultrasound beam transmitted from the array that results in a maximum representative signal value received from the region of interest;
   determine a second beam steering angle based on the first beam steering angle, the second beam steering angle being closer to perpendicular with the array than the first beam steering angle;
   acquire an ultrasound image using a beam transmitted from the array at the second beam steering angle;
   acquire a second ultrasound image using a beam transmitted from the array at a third beam steering angle, the third beam steering angle being closer to perpendicular with the array than the second beam steering angle; and
   combine the ultrasound image and the second ultrasound image to generate a third ultrasound image.

18. A system according to claim 17, wherein the region of interest is pre-set or defined by the user.

19. A system according to claim 17, wherein the representative signal value is one of mean, mode, median, percentile value or other statistical values.

20. A system according to claim 17, wherein determination of the first beam steering angle comprises varying a beam steering angle at a fixed angular increment or a variable angular increment.

21. A system according to claim 17, wherein the representative signal value is one of RF-signal, IF signal, demodulated baseband signal, line (i.e., beam) data, or scan-converted B-mode image signal.

22. A system according to claim 17, the processor-executable program code further to cause the system to:
   combine the ultrasound image and the second ultrasound image with weights.

23. A system according to claim 22, wherein the weights are dependent on the image pixel signals at each image pixel location.

24. A system according to claim 17, wherein determination of the first beam steering angle is based on the derivative of the representative signal value.

* * * * *